United States Patent [19]
Paez

[11] Patent Number: 4,791,916
[45] Date of Patent: Dec. 20, 1988

[54] SUSPENDED KNEE BRACE HAVING LIMITED RANGE OF MOTION HINGE
[75] Inventor: Juan B. Paez, Spring Arbor, Mich.
[73] Assignee: Camp International, Inc., Jackson, Mich.
[21] Appl. No.: 45,589
[22] Filed: May 4, 1987
[51] Int. Cl.[4] .......................... A61F 5/00; A61F 5/04
[52] U.S. Cl. .................... 128/80 C; 128/88; 128/80 F
[58] Field of Search ...................... 128/80 C, 88, 80 P

[56] References Cited

U.S. PATENT DOCUMENTS

| | | | |
|---|---|---|---|
| 2,558,986 | 7/1951 | Seelert | 128/80 F |
| 3,046,981 | 7/1962 | Biggs, Jr. et al. | 128/80 C |
| 3,528,412 | 9/1970 | McDavid | 128/80 |
| 3,817,244 | 6/1974 | Taylor | 128/80 |
| 3,826,251 | 7/1974 | Ross | 128/80 |
| 4,340,041 | 7/1982 | Frank | 128/80 C |
| 4,361,142 | 11/1982 | Lewis et al. | 128/80 C |
| 4,372,298 | 2/1983 | Lerman | 128/80 C |
| 4,506,661 | 3/1985 | Foster | 128/80 C |
| 4,599,748 | 7/1986 | Garcia | 128/80 C |
| 4,599,998 | 7/1986 | Castillo | 128/77 |
| 4,607,628 | 8/1986 | Dashetsky | 128/80 C |
| 4,681,097 | 7/1987 | Ponsiera | 128/88 |

FOREIGN PATENT DOCUMENTS 3416231 11/1985 Fed. Rep. of Germany .... 128/80 C

Primary Examiner—Edgar S. Burr
Assistant Examiner—Tonya Lamb
Attorney, Agent, or Firm—Beaman & Beaman

[57] ABSTRACT

A brace for the knee utilizing a flexible cage tightly wrapped about the knee from which the brace structure is suspended and utilizing polycentric hinges at the cage lateral regions including arms having controlled ranges of pivotal movement, the upper hinge arms being attached to a cup embracing the thigh and the lower hinge arms attaching to a cuff affixed to the lower leg. Straps drawing the cage tightly to the knee affixed to the cuffs suspend the brace from the cage, and the polycentric hinges accurately control the extent of leg flexion and extension. The hinge arms are interconnected through a gear and rack relationship, and stops associated with the rack limit arm movement.

11 Claims, 4 Drawing Sheets

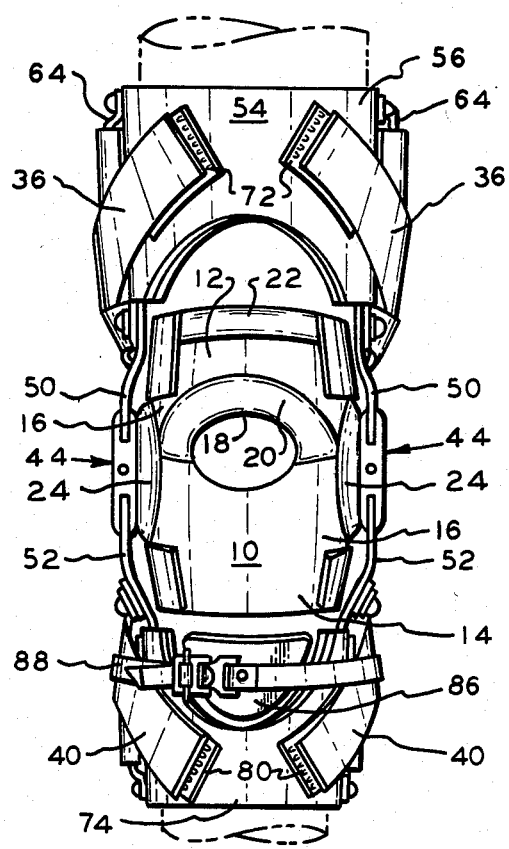
FIG. 1.
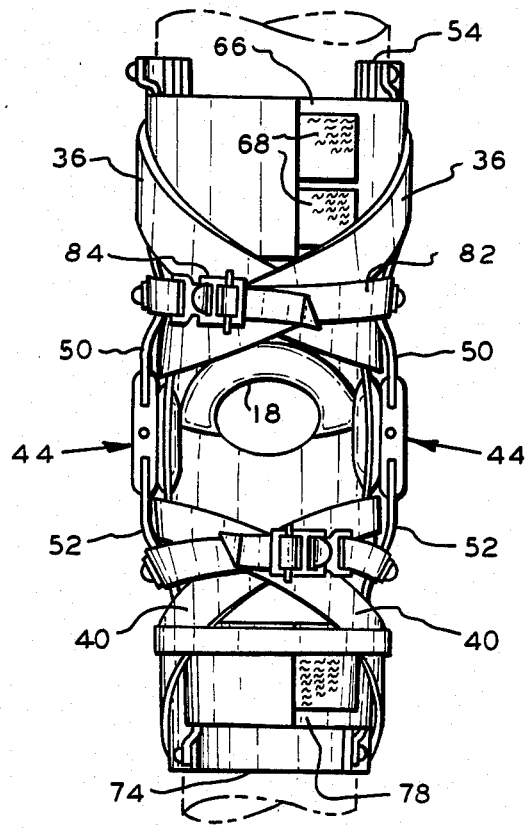

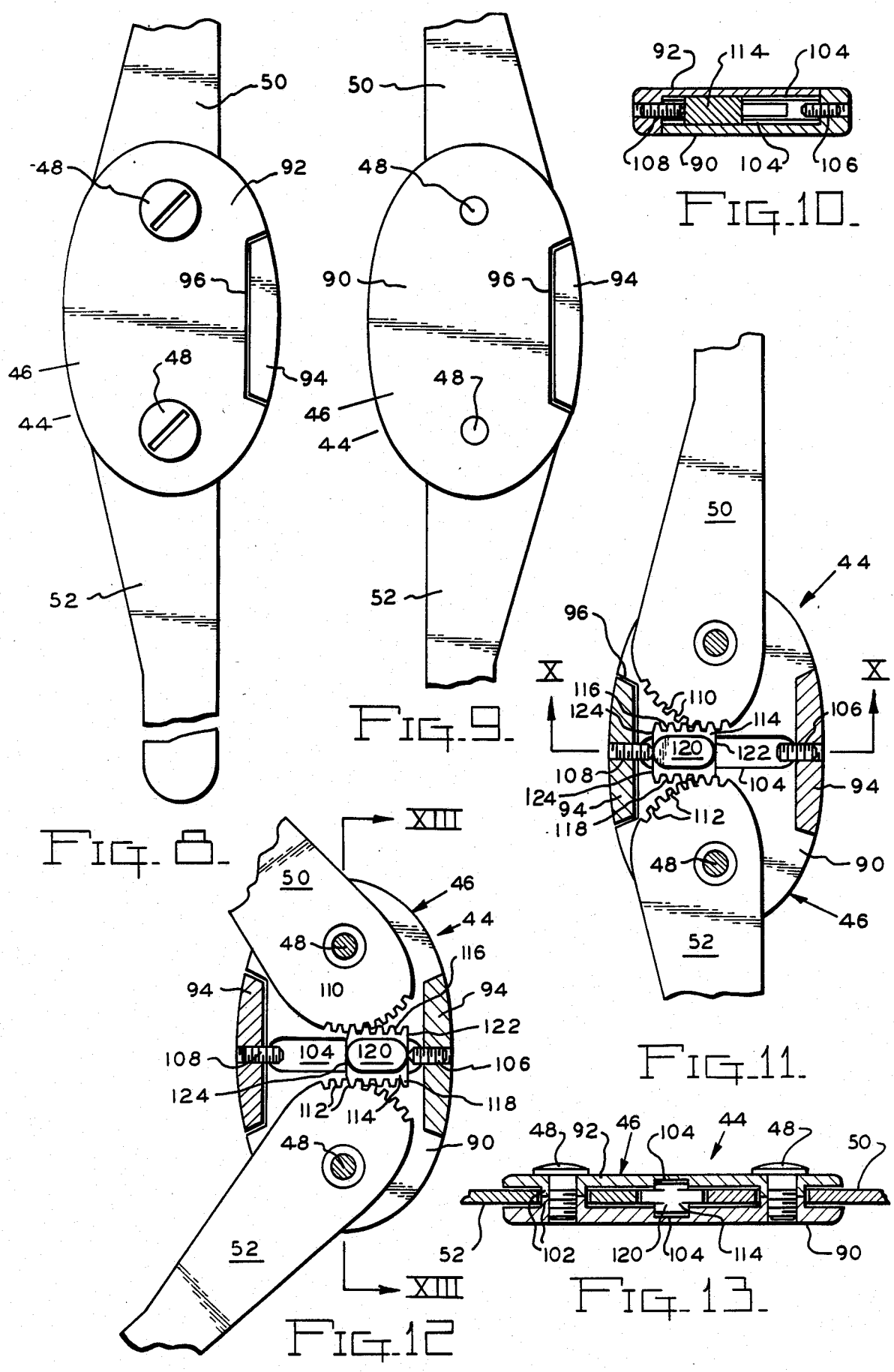

SUSPENDED KNEE BRACE HAVING LIMITED RANGE OF MOTION HINGE

BACKGROUND OF THE INVENTION

Knee braces are utilized to provide additional support to the knee wherein such support is desirous because of knee instability due to surgery, deformity, or the like, and knee braces are also commonly employed by athletes to protect against injury or provide additional support to a weakened knee joint. Knee braces may merely consist of an elastic sheath surrounding the knee, or the brace may be of a complicated nature utilizing a plurality of structural elements engaging the leg at the knee, and providing support above and below the knee joint.

In those knee braces of relatively complex construction for providing maximum knee support, it is known to engage the knee adjacent the joint utilizing hinge elements at the lateral portions of the knee and employ leg embracing collars or cuffs at the thigh and shin associated with the hinge wherein relative pivoting of the hinge arms is controlled to limit flexing and extension of the leg at the knee joint. A typical example of such apparatus is shown in U.S. Pat. No. 4,372,298.

Knee braces of the aforementioned type have the common deficiency of not maintaining the desired position on the leg. The knee brace will tend to "ride up" or "drop" relative to the knee causing the hinge to be misaligned to the knee and reducing the effectiveness of the brace, and in extreme instances, rendering the brace ineffective and a hindrance to limb movement.

Also, polycentric hinges used with knee braces having stop structure for regulating and limiting the extent of pivoting of the hinge arms or hinge elements have difficulty in maintaining the original adjustment controlling the degree of hinge movement which regulates flexing and extension. Relatively high forces are imposed upon the hinge arms during use and stops utilizing friction for positioning are ineffective to maintain the desired adjustment over extended periods of time and the stop structure of known non-friction stop hinges such as shown in U.S. Pat. No. 4,599,998 will not maintain the original setting.

It is an object of the invention to provide a knee brace which utilizes a flexible cage tightly strapped to the knee in such a manner that the cage is firmly and accurately positioned to the knee and will not shift relative to the knee during use.

A further object of the invention is to provide a knee brace having a flexible knee cage accurately positionable and maintainable with respect to the knee and wherein the brace includes upper and lower leg embracing cuffs which are suspended from the cage and utilize the permanent positioning of the cage to determine and maintain their position with respect to the associated portion of the leg.

Yet a further object of the invention is to provide a knee brace having upper and lower leg embracing members which are suspended from a flexible knee cage encompassing the knee and positioned thereto wherein straps tightening the flexible knee cage to the knee are also attached to the leg members in such a manner as to improve stability of the brace upon the leg without significantly interfering with leg movement and bending of the knee joint.

Additionally, an object of the invention is to provide a knee brace having a polycentric hinge located at each lateral portion of the knee, the hinge utilizing arms pivotally related to each other and including range of pivotal motion limiting structure having adjustable stops wherein the original positioning of the stops is accurately maintained over extended periods of time and will not be inadvertently changed due to the normal forces applied thereto during use.

Yet another object of the invention is to provide hinge structure for a knee brace having a body upon which the inner ends of hinge arms are pivotally mounted, gear teeth being defined upon the arms' inner ends concentric to the associated arm pivot axis, and a displaceable gear rack being located between the arms' inner ends meshing with the arms' gear teeth thereby interconnecting the arms to produce simultaneous pivotal movement. Adjustable stops in the form of screws are threaded into the body in alignment with the ends of the rack and the rack movement wherein a positive abutment between the rack and adjustment screws takes place to limit arm pivoting and the angular relationship of the hinge arms may be accurately controlled and maintained.

In the practice of the invention a flexible knee cage encompasses the anterior and lateral portions of the knee. The knee cage is formed of a flexible resilient material and includes a central opening receiving the patella. The upper front portion of the cage includes a reinforced area which wraps about the superior edge of the knee and the lateral cage portions are provided with condyle pads located inwardly of the hinges that are affixed thereto. Inelastic straps are attached to the upper and lower lateral portions of the knee cage for pulling the knee cage snugly into engagement with the knee.

A limited range of motion hinge is affixed to each lateral portion of the cage exteriorly of the lateral condyle pads. The hinge includes upwardly and downwardly extending arms, and the arms include inner ends separately pivotally connected to the hinge body forming a polycentric arrangement. The arms' inner ends are formed with gear teeth concentric with the associated arm pivot and a gear rack interposed between the arms meshes with the gear teeth and is guided for linear displacement as the arms pivot. Adjustable stops affixed to the hinge body in alignment with the ends of the rack engage the rack ends to limit the rack movement as the arms pivot to regulate the relative extent of arm pivoting.

An upper relatively rigid cuff of a U-configuration is mounted upon the outer ends of the upper hinge arms, and a lower cuff of U-configuration is similarly attached to the outer ends of the hinge lower arms. The upper and lower cuffs include an outer relatively rigid layer of synthetic plastic material on an inner soft foam liner, and an elastic strap bridges the lateral edges of the cuffs wherein the upper cuff encircles the thigh above the knee, while the lower cuff encircles the leg shin below the knee joint.

Strap fasteners in the form of hook or loop patches such as available under the trademark Velcro are mounted on the cuffs for cooperation with Velcro material defined on the knee cage straps. Thus, the upper portion of the knee cage can be drawn firmly into engagement with the knee by the associated upper straps and the tension in the straps is maintained by affixing the crossed outer strap ends to the upper cuff. Likewise, the nonelastic straps attached to the lower region of the knee cage are crossed at the back of the leg and pulled tight for attachment of the strap outer ends to the lower cuff. In this manner the knee cage is firmly located upon the knee wherein the upper and lower cuffs can be considered to be "suspended" from the cage.

A de-rotator shin-engaging plate is, preferably, located intermediate the lower cuff and the knee cage and is strapped to the lower region of the brace to reduce rotation of the tibia.

The hinge located at each lateral portion of the knee cage is formed by a plurality of plates receiving the inner ends of the hinge arms therebetween. The plates include bosses into which threaded stop screws are received which are in alignment with the ends of the rack located between the arms' inner ends. By regulating the longitudinal position of the stop screws the end of the screws can be positioned as desired and will engage the rack ends in a positive abutment manner wherein the force of the rack is longitudinal to the screw length. A hinge constructed in accord with the invention is capable of accurately limiting and maintaining angular relationships between the arms mounted on a common body, and although relatively high forces may be imposed upon the stops, the use of the rack and the abutment of the rack with the threaded stop screws insures consistent adjustment and control of the range of pivotal motion of the hinge arms over indefinite duration.

BRIEF DESCRIPTION OF THE DRAWINGS

The aforementioned objects and advantages of the invention will be appreciated from the following description and accompanying drawings wherein:

FIG. 1 is a front view of a knee brace constructed in accord with the invention as mounted upon a leg, FIG. 2 is a rear, elevational view of the brace as attached to the leg, FIG. 8 is an elevational view of one side of the hinge body, FIG. 9 is an elevational view of the other side of the hinge body, FIG. 10 is a sectional view as taken through the hinge rack along Section X—X of FIG. 11, FIG. 11 is an elevational view of the hinge illustrating the arms in an extension position, the hinge plate portion closest to the viewer being removed for purpose of illustration, FIG. 12 is a view similar to FIG. 11 illustrating the relationship of the components with the hinge arms in a maximum flexion position, and FIG. 13 is an elevational, sectional view as taken along Section XIII—XIII of FIG. 12.

DESCRIPTION OF THE PREFERRED EMBODIMENT

Figure 3:
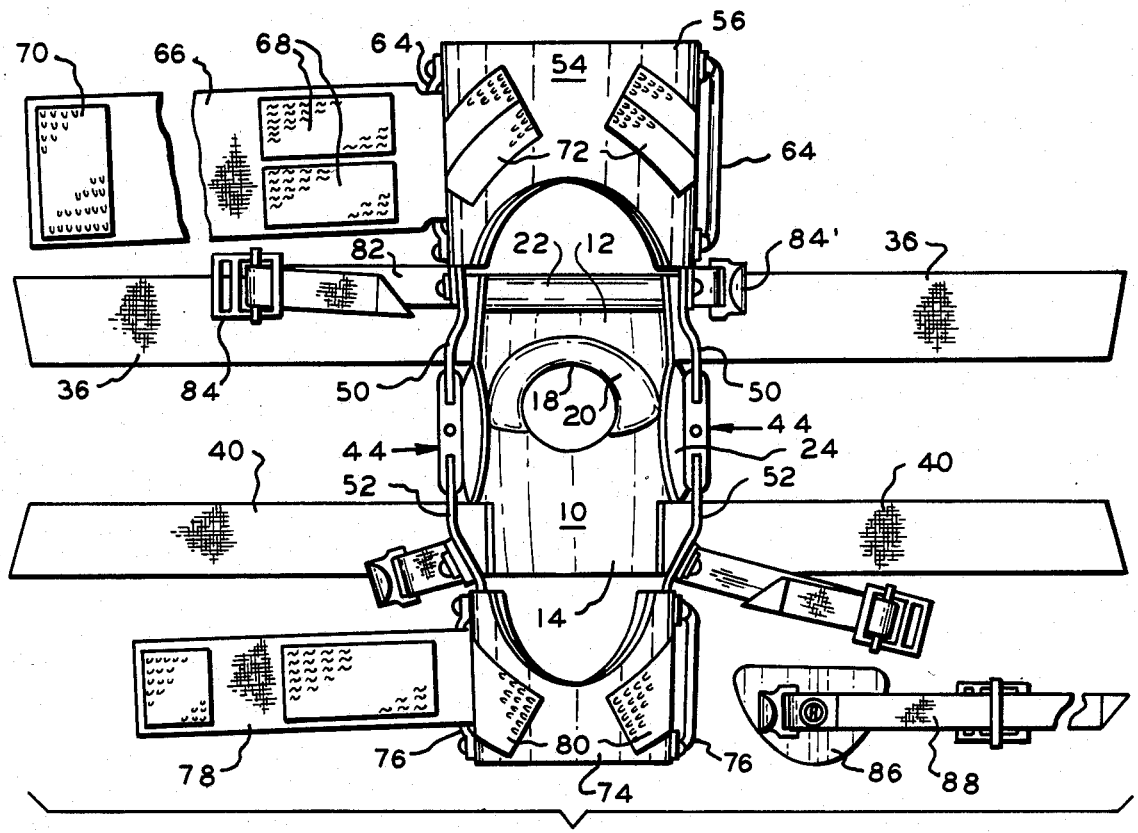
FIG. 3 is a front, elevational view of the knee brace, per se, shown in an opened condition.

A knee brace constructed in accord with the invention is best appreciated from FIGS. 1-5. The primary component of the brace comprises the knee cage 10 which is formed of a rubber or neoprene material having an outer elastic fabric layer bonded thereto. The cage material is flexible and stiffly resilient, and is of a generally U-shaped configuration having an upper region 12, a lower region 14 and lateral portions 16.

The knee cage is provided with a patella opening 18 intermediate the lateral portions for receiving the wearer's patella which aids in positioning the cage on the knee. Immediately above the opening 18 a crescent portion 20 of a thickened resilient material is added to the cage to provide additional protection and suspension adjacent the patella, and along the upper marginal edge the cage material is folded over to produce a doubly thick hem 22 which is pulled about the upper proximal edge of the knee for permitting the upper region to be wrapped tightly around the femoral condyle of the knee for maximum support and suspension.

Figure 7:
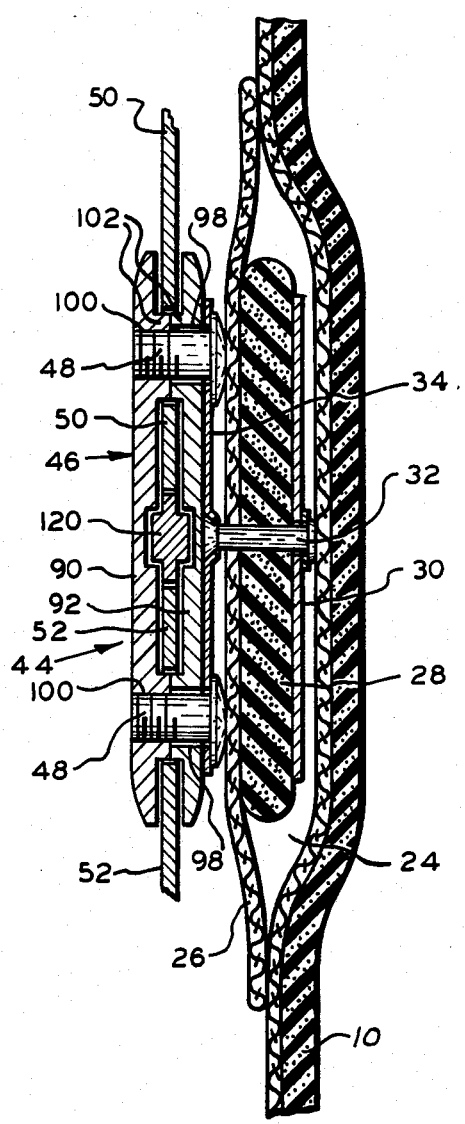
FIG. 7 is an enlarged, sectional view as taken through the knee cage lateral region and adjacent hinge along Section VII—VI of FIG. 5.

At its lateral central portions the knee cage 10 is provided with a pocket 24, FIG. 7, defined by the nylon-bonded neoprene cover 26 which is sewn to the cage lateral portion and a medium density synthetic foam condyle pad 28 is located within the pocket. An anchoring plate 30 is disposed along the inner side of the foam pad 28 and an aluminum rivet 32 extends through the foam and plate is headed over as apparent in FIG. 7. The outer end of the rivet 32 is of a conical configuration for attachment to the hinge mounting plate 34 as later described.

Figure 4:
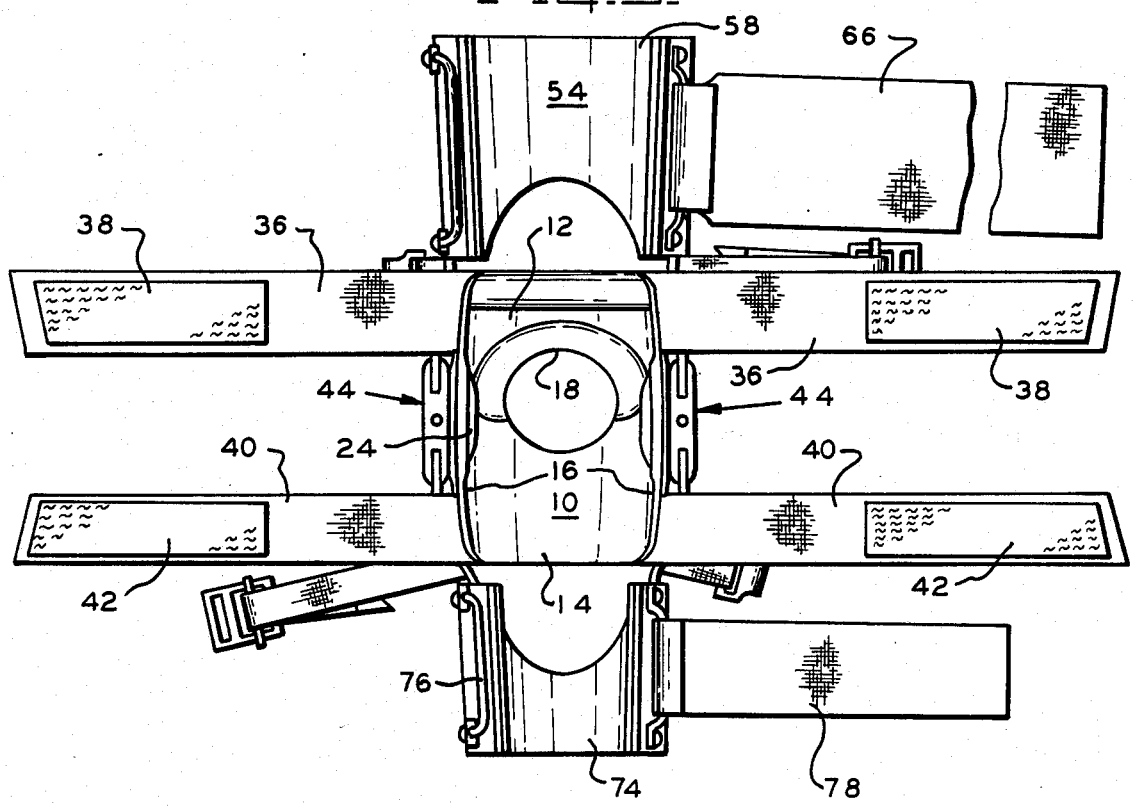
FIG. 4 is a rear, elevational view of the brace shown in the open position.
Figure 5:
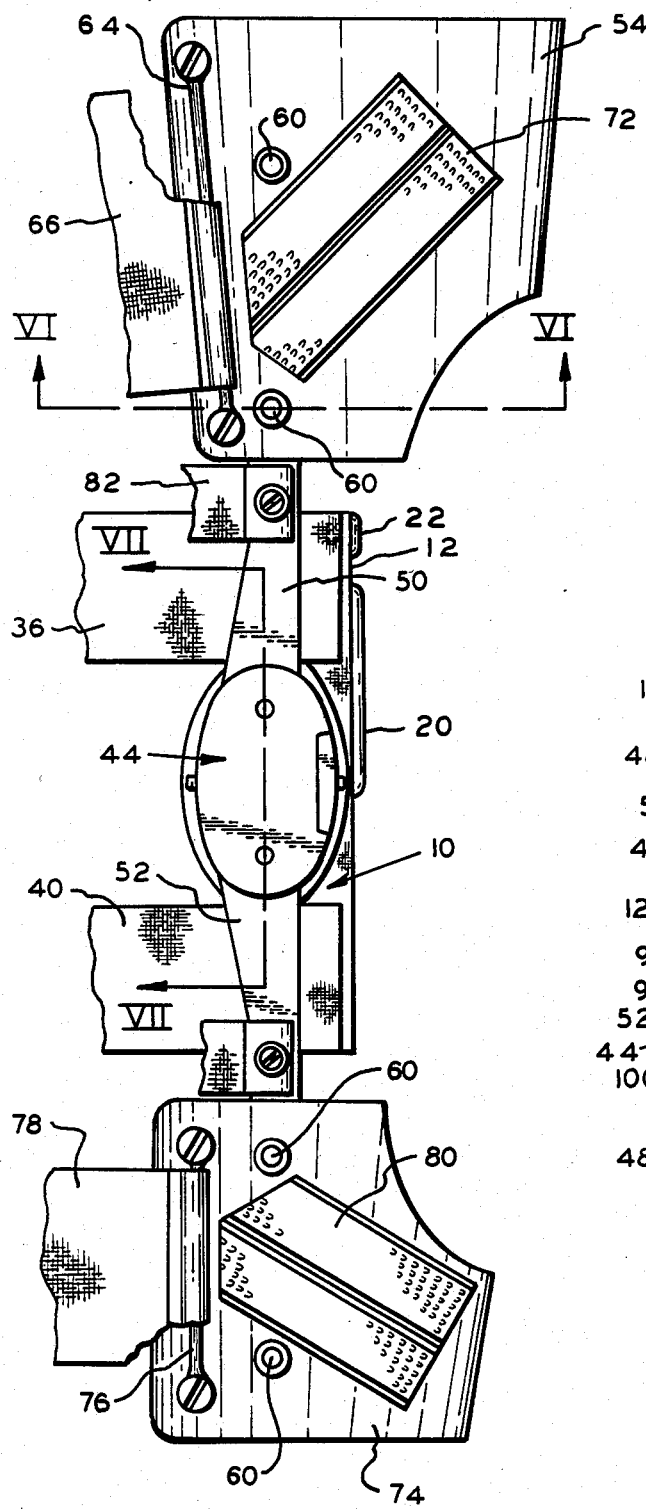
FIG. 5 is a right side, elevational view of the brace illustrating the knee cage, upper cuff, lower cuff, and end portions of the straps being omitted for purpose of illustration.

Flexible and stretchable straps 36 are attached to the upper region of the cage, as will be appreciated from FIGS. 3 and 4. The inner ends of the straps 36 are sewn to the lateral edges of the knee cage adjacent the upper region thereof, and the straps are provided with fastening means such as the loop material patches 38 commonly sold under the trademark "VELCRO", Likewise, a pair of flexible and stretchable straps 40 are sewn at one end to the lower region of the cage 10 adjacent the lateral edges thereof as appreciated from FIGS. 3 and 4, and the outer ends of the straps 48 are also provided with the "VELCRO" loop patches 42.

A limited range of motion hinge generally designated at 44 is attached to each of the central lateral regions of the knee cage at the condyle pads and pockets 24. The hinges 44 each include a body 46 having spaced parallel pivots 48 defined therein which are in the form of screws. Each of the pivot screws 48 is associated with the inner end of a hinge arm. As will be appreciated from FIG. 7, the pivot screws 48 attach the hinge mounting plate 34 to the hinge body 46 and as the head of the rivet 32 is affixed to the plate 34 the plate will firmly affix the hinge 44 to the lateral portion of the knee cage at the adjacent condyle pocket.

Each of the hinges 44 includes an upper arm 50, and a lower arm 52, and as later described, the arms are interconnected for pivotal movement with respect to the body 46 through a predetermined range of motion.

Figure 6:
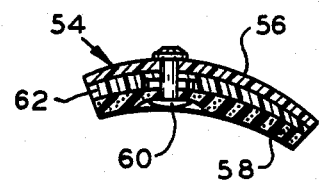
FIG. 6 is a detail, sectional, elevational view as taken through the lower region of the upper cuff along Section VI—VI of FIG. 5.

An upper cuff 54 is located above the knee cage 10 and is supported relative to the knee cage by the upper hinge arms 50. The cuff 54 is of a generally U-shaped configuration preferably consisting of a relatively rigid carbon composite material 56 having a soft foam inner layer 58 bonded thereto which may have an inner fabric cover. The configuration of the cuff 54 generally corresponds to the configuration of the thigh of the wearer, and as the cuff is open at the rear, it may be readily placed upon the thigh. As will be appreciated from FIG. 6, the upper ends of the hinge arms 50 extend into the cuff intermediate the rigid layer 56 and the soft layer 58 and are riveted thereto by rivets 60. In that the arms will produce a spacing between the outer and inner layers of the cuff, such spacing may be filled with an epoxy resin 62 as apparent in FIG. 6.

A wire rail 64 is affixed to the cuff 54 adjacent each rear lateral edge thereof, and an elastic band 66 is affixed to one of the rails 64 and includes loop "VELCRO" patches 68 and hook Velcro patches 70 whereby the free end of the band may be passed under the other rail 64 and folded upon itself and affixed thereto to confine the thigh within the leg and firmly mount the cuff on the thigh. "VELCRO" hook patches 72 are attached to the front outer portion of the cuff 54, as appreciated from FIG. 3, for cooperation with the free ends of straps 36 as later described.

The lower cuff 74 is attached to the hinge lower arms 52 by rivets in a manner similar to the upper cuff 50, and the lower cuff 74 is also of a U-shaped configuration and of smaller dimension than the cuff 54 as to closely fit upon the lower leg and shin of the wearer. The U-shaped configuration of the cuff 74 permits the lower leg to be received within the cuff and the cuff 74 is of identical construction as compared to the upper cuff in that the outer layer is formed of a rigid carbon composite material lined with a soft foam and fabric. Rails 76 affixed to the rear lateral edges of the lower cuff permit the band 78 to be attached thereto, and the band includes "VELCRO" hook and loop patches wherein the free end of the band may be inserted under a rail 76 and folded upon itself and drawn snugly so that the cuff 74 will firmly encompass the wearer's lower leg. "VELCRO" hook patches 80 are attached to the front of the cuff 74 as shown in FIG. 3 for cooperation with the free ends of the straps 40 as described below.

A strap 82 which is flexible but non-stretchable is affixed to the hinge upper arms 50 and includes buckles 84 and 84' whereby the strap will extend across the rear of the leg to prevent hyperextension of the knee with the extremity in the brace.

To mount the knee brace upon the wearer, the straps 36, 40 and 82 will be "opened" as illustrated in FIGS. 3 and 4, as will the bands 66 and 78. Thus, the wearer may insert the leg into the brace so that the knee cap is received within the opening 18 of the knee cage 10, the thigh is received within cuff 54, and the shin and lower leg within cuff 74.

Initially, the upper cuff 54 may be drawn into firm engagement with the thigh, and the thigh completely embraced by the cuff, by inserting the free end of the band 66 under a rail 64, tensioning the band and folding it back upon itself to interlock the "VELCRO" patches 68 and 70 and thereby "close" the upper cuff. In a like manner, the band 78 of the lower cuff 74 is inserted through the left rail 76, FIG. 4, and is tensioned and folded back upon itself and attached to close the cuff 74 upon the wearer's leg.

The straps 36 are then crossed at the rear of the leg and pulled tightly upwardly in a diagonal direction, FIG. 2, and the free ends of the straps are attached to the Velcro patches 72 affixed to the cuff 54. Because of the resilient nature of the knee cage, this firm tensioning of the straps 36 will tightly pull the double hem 22 about the upper proximal edge of the knee and prevent the knee cage, and brace, from sliding downwardly on the leg.

In a similar manner, the lower knee cage straps 40 are tightly tensioned to stretch and firmly draw the lower region of the knee cage into engagement with the lower region of the knee, and the straps 40 are crossed behind the wearer's leg and the strap free ends attached to the "VELCRO" patches 80 affixed to the lower cuff 74.

The strap 82 may now be connected to the buckles 84 and 84' and tensioned, which will prevent hyperextension of the leg.

A de-rotation pad 86 may be optionally employed with the brace, and in the figures is illustrated. The de-rotation pad 86 includes a pad formed similar to the cuffs 54 and 74 being of a substantially rigid synthetic plastic outer cover having an inner foam layer. The pad 86 is of a V-configuration to conform to the shin, and a buckled strap 88 mounted upon the pad passe about the brace and aids in preventing relative rotation of the leg tibia within the brace.

With the brace mounted as described, the primary support component is the knee cage 10 which firmly positions the knee cage relative to the knee. The firm interrelationship between the double hem 22 and the upper proximal edge of the knee prevents the knee cage from moving downwardly, and this positioning of the cage is enhanced by the reception of the knee cap within the opening 18 and the firm support provided by the thickened crescent portion 20 located above the knee cap. As the upper arms 50 of the hinges 44 locate the upper cuff 54 to the knee cage, and as the hinge lower arms 52 locate the lower cuff 74 to the knee cage, the cuffs are considered to be "suspended" from the knee cage and a brace so constructed will maintain its desired position on the leg and will not "work" downwardly as the leg is flexed. This type of brace controls medial lateral instabilities, anterior cruciate ligament instabilities and rotary combined instabilities. The presence of the condyle pads and pockets and the hinges at the lateral regions of the knee protect the knee from lateral forces or impacts during sports, and as the angular relationships between the arms 50 and 52 of each hinge may be accurately controlled and limited, as later described, the knee brace prevents excessive flexion and extension of the knee.

The hinges 44 are identical and their construction will be appreciated from FIGS. 7-13.

The hinge body 46 is formed of a pair of plates 90 and 92 which are substantially identical. Each plate is of a generally elliptical configuration and along a lateral edge includes an upstanding boss 94. The other lateral edge of each plate is formed with a recess 96 of a configuration similar to the boss whereby the two plates may be interlocked as the boss 94 of one is received within the recess 96 of the other. The plates 90 and 92 are usually formed of metal, such as aluminum, but may be formed of a high-strength synthetic plastic material. The plate 92 is formed with openings 98 for receiving the pivot screws 48 while the plate 90 includes threaded openings 100 for cooperating with the threads of the pivot screws 48, FIG. 7. The screws 48 maintain the plates in parallel assembled relationship and the interior of the plates is accessible through the slots defined at the ends of the plates. The spacing between the plates is determined by the engagement of the annular bosses 102 surrounding the openings 98 and 100 as will be apparent from FIG. 7.

Each of the hinge plates is formed with an elongated guide slot 104 of linear configuration and when the plates are assembled by the pivot screws the guide slots will be in opposed parallel relationship together defining a rack guide. Also, each boss 94 is provided with a threaded opening for receiving an abutment stop screw 106 or 108 therein. The screws 106 and 108 are of sufficient length to extend inwardly of the associated boss for positioning of the inner end between the guide slots and at their outer ends the stop screws include hexagonal recesses for receiving a standard Allen wrench.

The inner end of the upper arm 50 is provided with a set of gear teeth 110 which are concentric with the axis of the associated pivot screw 48, and in a like manner, the inner end of the lower arm 52 is provided with a set of gear teeth 112 concentric with its associated pivot screw.

A gear rack 114 is located between the gear teeth sets 110 and 112 and includes teeth 116 which mesh with teeth 110 while rack teeth 118 mesh with teeth 112. The rack includes a projection 120 defined upon each side thereof which is received within a body guide slot 104, and in this manner the rack is guided for linear movement within the body 46. The rack 114 also includes an end 122 and an end 124, the end 122 being in alignment with the stop screw 106 while the end 124 aligns with the stop screw 108, as apparent from FIGS. 11 and 12.

With the hinge components assembled as will be appreciated from the drawings, the arms 50 and 52 are interconnected by the gear teeth sets 110 and 112 and the rack 114 wherein pivoting of one arm will pivot the other in the opposite direction. Such pivoting of the arms will cause a linear translation of the rack 114 back and forth in the guide slots 104 displacing the rack either toward the stop screw 106 or the screw 108.

It will be appreciated that as the pivoting of the hinge arms occurs due to the bending of the knee, the rack 114 will approach the set screw 106 as the knee is flexed and the angle between the arms 50 and 52 decreases, as shown in FIG. 12. This flexing angle will be terminated upon engagement of the rack end 122 with the screw 106 as shown in FIG. 12. Conversely, as the knee is extended and the angle between the arms 50 and 52 increases, the rack 114 will be moved to the left, FIG. 11, and the rack end 124 will engage the end of the screw 108 controlling the amount of the extension angle permitted. Merely by adjusting the extent which the screws 106 and 108 extend toward the rack 114 the angles of flexion and extension of the hinge may be very accurately controlled.

As the linear movement of the rack 114 is parallel to the length of the stop screws 106 and 108, the termination of movement of the hinge is not dependent upon "frictional" stops, but rather a positive abutment is produced wherein the force imposed by the rack as it engages an abutment screw will be parallel to the length of the abutment screw placing the threads under compression. Preferably, the abutment screws 106 and 108 include nylon inserts or other known friction-producing elements which will prevent inadvertent rotation of the abutment screws due to vibration, and once the hinge of the invention is adjusted for maximum angles of flexion and extension, these adjustments will not vary until the screws are purposely rotated and relocated by the technician.

It will therefore be appreciated from the above description that the invention is directed to a knee brace capable of providing extensive support of the knee wherein the brace ill be firmly located upon the leg and will not inadvertently move relative thereto. The use of the limited range of motion hinges prevents excessive flexing or extension of the knee and the construction of the hinges and the adjustments thereof will be maintained during use.

It is appreciated that various modifications to the inventive concepts may be apparent to those skilled in the art without departing from the spirit and scope of the invention.

I claim:

1. A knee brace characterized by its stability of positioning upon the leg utilizing the knee structure for locating and suspending the brace comprising, in combination, a flexible knee cage, said knee cage being formed of a flexible elastomeric material of a U-configuration having an open rear portion, upper, lower and central regions, an outer surface, an inner surface and right and left lateral portions, a continuous circumference patella receiving opening defined in said cage central region, first tension means affixed to said cage upper region for drawing said cage upper region into firm engagement with the upper edge of the knee, second tension means affixed to said cage lower region for drawing said cage lower region into firm engagement with the lower edge of the knee, a condyle pad defined upon each cage lateral portion adapted to support a lateral portion of the knee, a hinge mounted upon each condyle pad adjacent said cage outer surface, an upper cuff located above said cage adapted to encircle the wearer's thigh, a lower cuff located below said cage adapted to encircle the wearer's leg below the knee, right and left lateral portions defined upon said upper and lower cuffs, said first tension means comprising first and second straps each having a lower end attached to a cage upper region lateral portion and an upper end attached to said upper cuff, and said second tension means comprising third and fourth straps each having an upper end attached to a cage lower region lateral portion and a lower end attached to said lower cuff, each hinge including a body and elongated upper and lower arms pivotally mounted upon said body and extending therefrom, said hinge's upper arms being fixed to said upper cuff's lateral portions, and said hinge's lower arms being fixed to said lower cuff's lateral portions.

2. In a knee brace as in claim 1, said upper and lower cuffs being of a U-configuration each having an open rear portion, said cuffs having an outer cover of substantially rigid material and a soft inner liner, an elastic band being disposed across the open rear portion of each of said cuffs.

3. In a knee brace as in claim 1, arm motion limiting means defined on said hinge body limiting the extent of pivoting of said upper and lower arm relative to said body and to each other to control knee flexion and extension.

4. In a knee brace as in claim 3, said hinge arms each including an inner end pivotally connected to said hinge body, said motion limiting means including gear teeth defined upon said arms' inner ends, a toothed gear rack meshing with the gears of said arms whereby pivoting of said arms linearly translates said rack, and adjustable stops defined on said body engagable by said rack limiting pivotal movement of said arms.

5. A knee brace characterized by its stability of positioning upon the leg utilizing the knee structure for locating and suspending the brace comprising, in combination, a flexible knee cage having upper, lower and central regions, an outer surface, an inner surface and right and left lateral portions, patella receiving means defined in said cage central region, first tension means affixed to said cage upper region for drawing said cage upper region into firm engagement with the upper edge of the knee, second tension means affixed to said cage lower region for drawing said cage lower region into firm engagement with the lower edge of the knee, a condyle pad defined upon each cage lateral portion adapted to support a lateral portion of the knee, a hinge mounted upon each condyle pad adjacent said cage outer surface, an upper cuff located above said cage adapted to encircle the wearer's thigh, a lower cuff located below said cage adapted to encircle the wearer's leg below the knee, right and left lateral portions defined upon said upper and lower cuffs, each hinge including a body and elongated upper and lower arms pivotally mounted upon said body and extending therefrom, said hinge's upper arms being fixed to said upper cuff's lateral portions, and said hinge's lower arms being fixed to said lower cuff's lateral portions, said first tension means comprising first and second straps each having a lower end attached to a cage upper region lateral portion and an upper end attached to said upper cuff, and said second tension means comprising third and fourth straps each having an upper end attached to a cage lower region lateral portion and a lower end attached to said lower cuff, said first and second straps' lower ends being connected to said cage right and left lateral portions, respectively, and said first and second straps' upper ends being connected to said upper cuff's left and right lateral portions, respectively, said third and fourth straps' upper ends being connected to said cage right and left lateral portions, respectively, and said third and fourth straps' lower ends being connected to said lower cuffs, left and right lateral portions, respectively.

6. In a knee brace as in claim 5, hook fasteners mounted on said lateral portions of said cuffs and loop fasteners adapted to connect to said loop fasteners defined upon said upper ends of said first and second straps and said lower ends of said third and fourth straps.

7. A limited range of motion hinge for an orthopedic knee brace comprising, in combination, a body, first and second arms each having an outer end, and an inner end independently pivotally mounted upon said body, gear teeth defined on said inner ends of said arms, a movable toothed rack located on said body between the inner ends of said arms in mesh with the gear teeth of both arms whereby pivoting of said arms translates said rack said rack having a projection on each side, guide means defined on said body including a pair of slots guiding said rack during translation, said projections being received in said slots, ends defined upon said rack, and at least one threaded stop threaded directly through said body in alignment with said rack and engagable by one of said rack ends to limit rack movement and the extent of pivoting of said arms, said stop being adjustable in the direction of said rack.

8. In a hinge for an orthopedic knee brace as in claim 7, said stop comprising a threaded screw.

9. In a hinge for an orthopedic knee brace as in claim 7, a pair of threaded stops threaded into said body in spaced opposed relation, said rack being located between said stops and each rack end being selectively engagable with one of said stops.

10. In a hinge for an orthopedic knee brace as in claim 9, said stops comprising threaded screws.

11. A limited range of motion hinge for an orthopedic knee brace comprising, in combination, a body having a pair of slots, first and second elongated arms each having inner and outer ends, first and second parallel spaced pivots mounted upon said body, said first and second arms' inner ends being mounted on said first and second pivots, respectively, whereby said arms' inner ends are in spaced relationship to each other, first and second sets of gear teeth defined upon said first and second arms inner ends, respectively, said sets of gear teeth being in spaced opposed relation to each other and each set being concentric to the pivot of the associated arm, a toothed rack having ends and two sides with a projection on each side, each projection mounted in one of said slots of said body for sliding movement thereon in opposed directions, said rack being located between said sets of gears and meshing with the teeth thereof, and threaded screws directly threaded through said body in alignment with said rack adapted to be engaged by a rack end to limit pivoting of said arms relative to each other.

* * * * *